US007569023B2

(12) United States Patent
Dobbs

(10) Patent No.: US 7,569,023 B2
(45) Date of Patent: Aug. 4, 2009

(54) ORTHOTIC CLUBFOOT DEVICE

(75) Inventor: Matthew Dobbs, St. Louis, MO (US)

(73) Assignee: Washington University, St. Louis, MO (US)

( * ) Notice: Subject to any disclaimer, the term of this patent is extended or adjusted under 35 U.S.C. 154(b) by 218 days.

(21) Appl. No.: 11/426,376

(22) Filed: Jun. 26, 2006

(65) Prior Publication Data

US 2007/0088240 A1    Apr. 19, 2007

Related U.S. Application Data

(60) Provisional application No. 60/696,262, filed on Jul. 1, 2005.

(51) Int. Cl.
A61F 5/00 (2006.01)
(52) U.S. Cl. .......................................... 602/29; 602/23
(58) Field of Classification Search .................. 602/23, 602/24, 28–29, 5; 36/140–144, 148, 158, 36/168
See application file for complete search history.

(56) References Cited

U.S. PATENT DOCUMENTS

| 2,906,261 | A | 9/1959 | Craig |
| 3,171,407 | A | 3/1965 | Rogers |
| 3,209,749 | A | 10/1965 | Walker |
| 3,777,747 | A | 12/1973 | Friedman |
| 4,429,523 | A | 2/1981 | Birdwell |
| 4,481,940 | A | 11/1984 | Kurtz et al. |
| 5,700,237 | A | 12/1997 | Hess |
| 5,797,862 | A | 8/1998 | Lamont |
| 5,921,945 | A | 7/1999 | Gray |
| 2007/0142760 | A1 | 6/2007 | Mitchell |

OTHER PUBLICATIONS http://hortontechnology.com/click.html, Horton Click, The new generation of foot rotation bars, dated Sep. 22, 2006.
Dobbs, M. et al., "Factors Predictive of Outcome After Use of the Ponseti Method for the Treatment of Idiopathic Clubfeet" The Journal of Bone & Joint Surgery, vol. 86-1, No. 1, Jan. 2004, pp. 22-27.

*Primary Examiner*—Kim M Lewis
(74) *Attorney, Agent, or Firm*—Polsinelli Shughart PC

(57) ABSTRACT

The present invention relates to an orthotic device wherein the patient's feet are maintained at a desired angle while allowing the patient to move in an otherwise normal manner and preventing blister formation. The orthotic device generally comprises an orthotic splint assembly, two ankle foot orthosis and two custom molded inserts secured to the ankle foot orthosis.

14 Claims, 6 Drawing Sheets

ORTHOTIC CLUBFOOT DEVICE

CROSS-REFERENCE TO RELATED APPLICATION

This application claims priority from Provisional Application Ser. No. 60/696,262 filed on Jul. 1, 2005, which is hereby incorporated by reference in its entirety.

FIELD OF THE INVENTION

The present invention relates to an orthotic device wherein a patient's feet are maintained at a desired angle while allowing the patient to move in an otherwise normal manner.

BACKGROUND OF THE INVENTION

It is known that clubfoot is one of the most common serious congenital deformities of the musculoskeletal system in newborns, with a frequency of 1 to 6 in 1000 in the Caucasian population. The foot has a typical appearance of pointing downwards and twisted inwards. Since the condition starts in the first trimester of pregnancy, the deformity is quite established at birth, and is often very rigid. There are three main types of defect: Equinovarus, Calcaneus valgus, and Metatarsus varus or adductus. Equinovarus is the most severe type of the defect, wherein the foot is twisted inward and downward so that the patient cannot place the insole flat on the ground and must walk on the ball, the side, or even the top of the foot. Calcaneus valgus is the moderately severe form of the defects, wherein the foot is angled upward and outward so that the patient has to walk on the heel or the inner side of the foot. Metatarsus varus or adductus is the mildest form of the defect, does not involve the ankle, but only the bones and connective tissues of the foot, causing the front part to turn inward.

The cause of the deformity is unknown. Irrespective of its causes, during development, the posterior and medial tendons and ligaments (in the back and inside) of the foot fail to keep pace with the development of the rest of the foot. As a result, these tendons and ligaments tether the posterior and medial parts of the foot down, causing the foot to point downwards and twist inwards. The bones of the feet, therefore, are held in an abnormal position. Over time, if uncorrected, the bones will become misshapen.

Clubfoot does not cause pain in the infant. Because it is so obvious, it is usually discovered at birth. If left untreated, the deformity persists. It worsens over time, with secondary bony changes developing over years. An uncorrected clubfoot in the older patient or adult is unsightly, and crippling. The patient walks on the outside of the foot, which is not meant for weight-bearing.

There are different treatment options for clubfoot, including serial casting, splints, the Ponsetti Method, and surgery. The Ponsetti Method includes casting, cutting of the Achilles tendon, and subsequently wearing corrective foot orthosis. Typically, the treatment involves weekly stretching of the foot deformity, followed by the application of long plaster leg casts. Before the application of the final leg cast, the physician usually performs a tenotomy, a percutaneous heel cord lengthening to correct the hindfoot deformity. The patient wears the final cast for three weeks to allow the tendon to heal. The patient then wears a corrective foot orthosis full time for three months, followed by night and naptime wear for up to four years to prevent the deformity from recurring.

Compliance with corrective foot orthosis is essential to prevent relapse of the clubfoot deformity. If the corrective foot orthosis is not worn, reocurrence generally is inevitable and the patient is faced with major reconstructive foot surgery to correct the clubfoot. Children that have the major surgery often suffer stiffness, pain, and arthritis in early adulthood.

The main reasons for noncompliance with corrective foot orthosis is that they limit the mobility of the patient, are uncomfortable, and/or form blisters on the back of the patient's heels. For example, one corrective foot orthosis includes a pair of shoes mounted on a flat bar. This corrective device is extremely uncomfortable because it maintains the feet in almost rigid positions. Another corrective foot orthosis includes a parallelogram link as a cross bar between the patient's feet. This corrective device, while allowing movement of each foot forwards and backwards, restricts freedom of movement of either foot up and down. Upward and downward movement is restricted with this type of device because articulation occurs in the middle of the cross brace rather than by the shoe or foot orthosis. In addition it does not address the blisters and friction created by the shoe on the patient.

It is thus desired to have a corrective foot orthosis device wherein a patient's feet are maintained at a desired angle while allowing the patient's feet to have vertical mobility and preventing blister formation.

SUMMARY OF THE INVENTION

Among several aspects of the invention is provided an orthotic splint assembly. The orthotic splint includes a rigid cross brace, a first right angle member connected to a first foot support, and a second right angle member connected to a second foot support. The first right angle member has one arm secured to the foot support and the other arm interconnected to the cross brace by a first pivot assembly. Similarly, the second right angle member has one arm secured to the foot support and the other arm interconnected to the cross brace by a second pivot assembly.

Still further is provided an orthotic device. The orthotic device, in addition to the orthotic splint assembly, includes an ankle foot orthosis connected to each foot support and a custom molded insert secured inside the ankle foot orthosis by a securing means.

Other aspects and features of this invention will be in part apparent and in part pointed out hereinafter.

DESCRIPTION OF THE PREFERRED EMBODIMENTS

The present invention provides an orthotic device, wherein a patient's feet are maintained at a desired angle while allowing the patient's feet to have vertical mobility and preventing blister formation. It has been discovered that a custom molded insert placed inside a standard ankle foot orthosis (AFO) prevents blister formation, pressure sores and discomfort previously encountered when wearing the standard braces. In addition, the orthotic device of the present invention includes an orthotic splint assembly that allows the patient's legs to move independently while maintaining the heels at approximately shoulder width. By maintaining this distance, the patient's knees are not injured or torqued. The present invention is also directed to an orthotic splint assembly including a cross brace, two foot supports connected to the cross brace by two pivot assemblies, which allow each foot support to swivel or pivot independently around a vertical axis.

Figure 1:
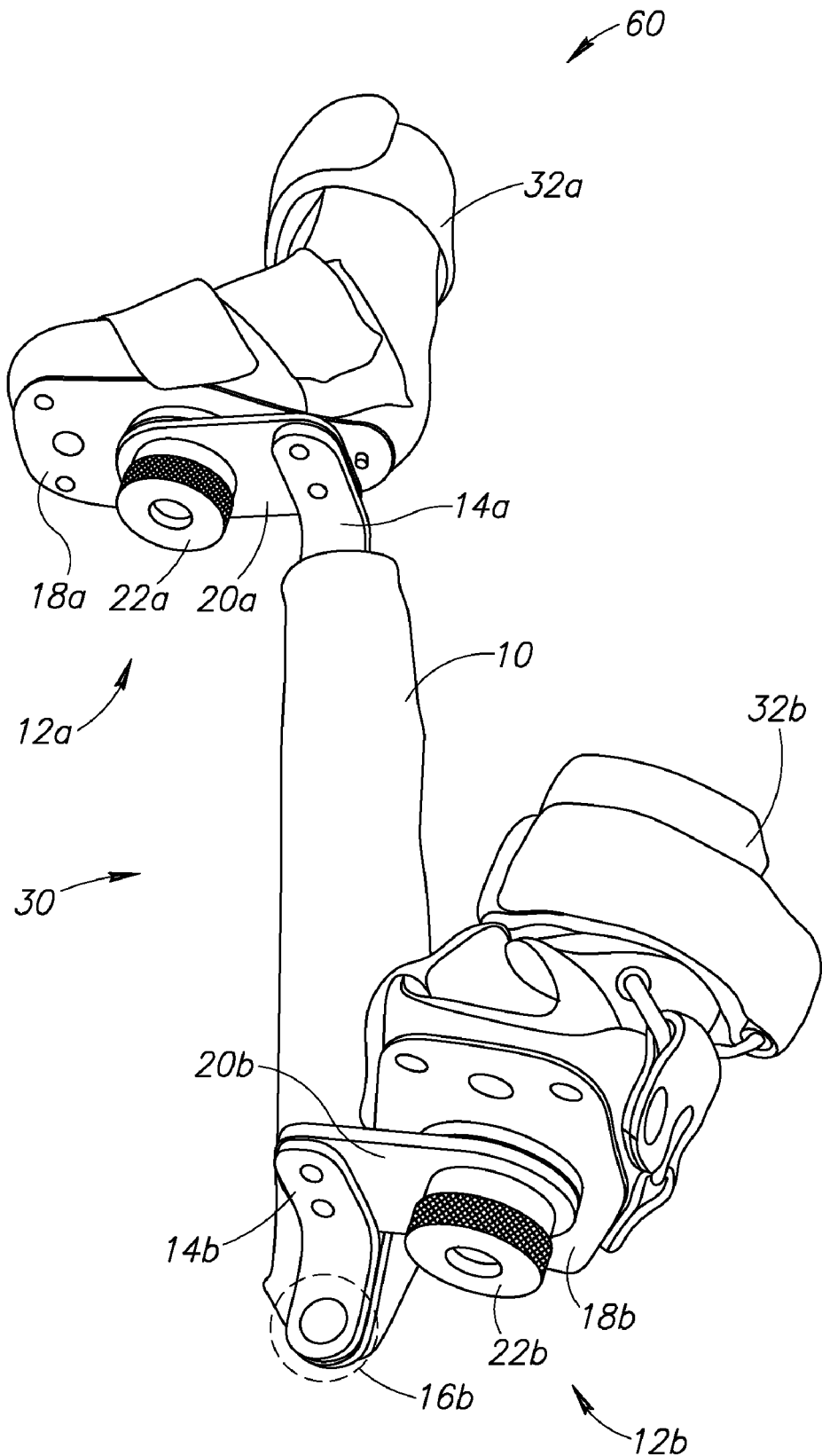
FIG. 1 is a perspective view of an embodiment of an orthotic device.
Figure 2:
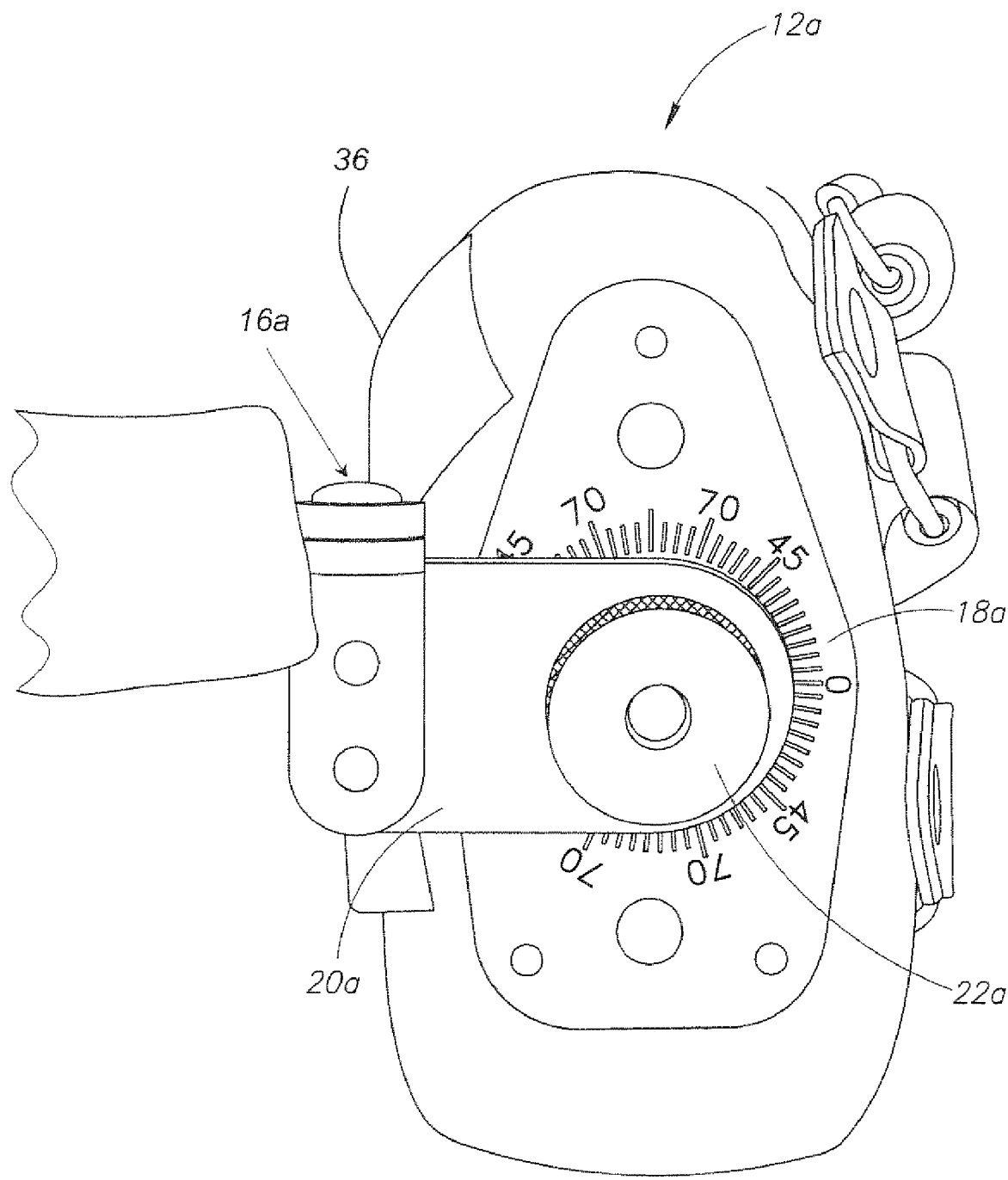
FIG. 2 is a perspective view of an embodiment of a foot support comprising an orthosis support, a support plate, and an adjusting member.
Figure 3:
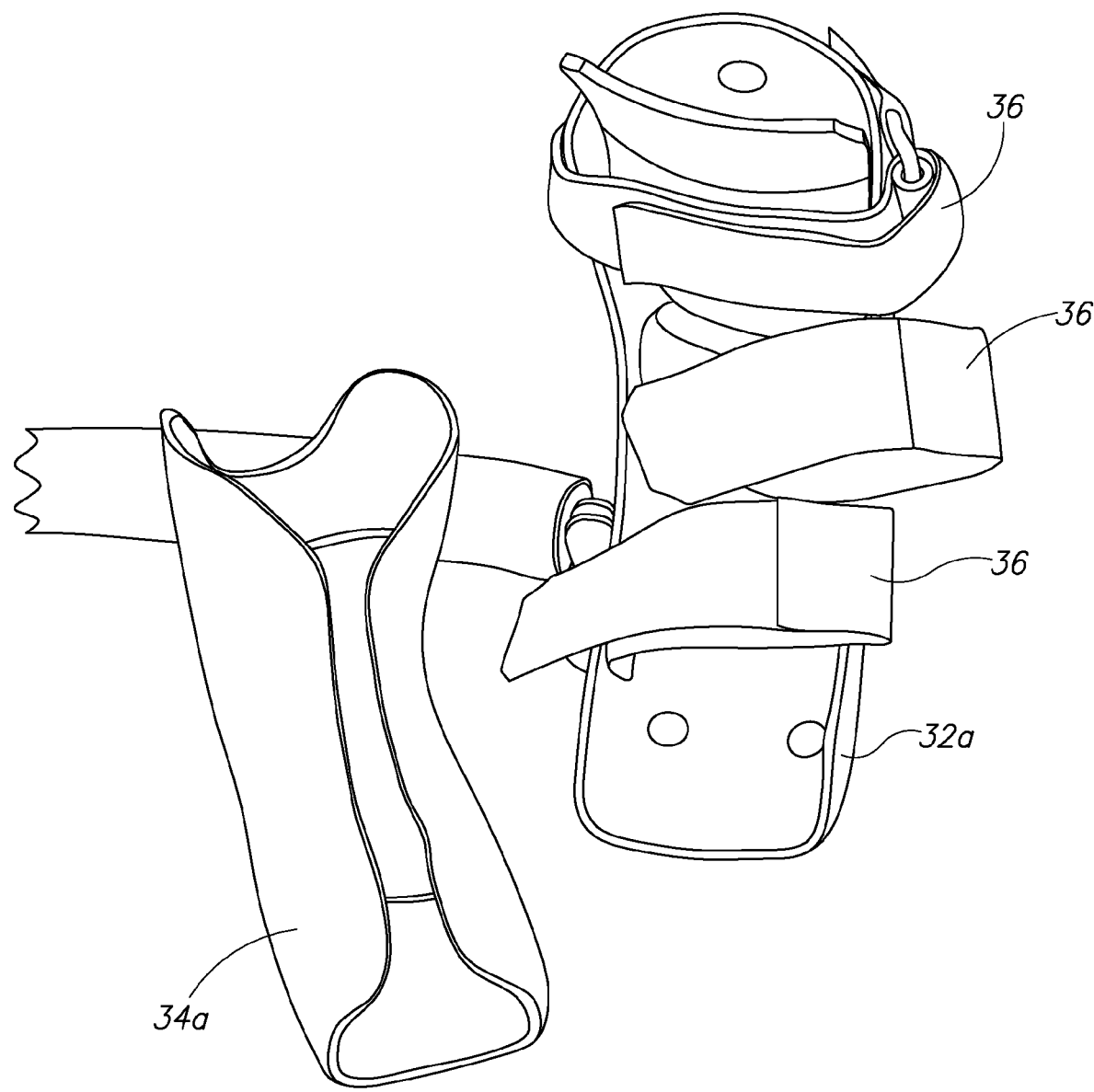
FIG. 3 is an expanded view of an ankle foot orthosis and the custom molded insert.
Figure 5A:
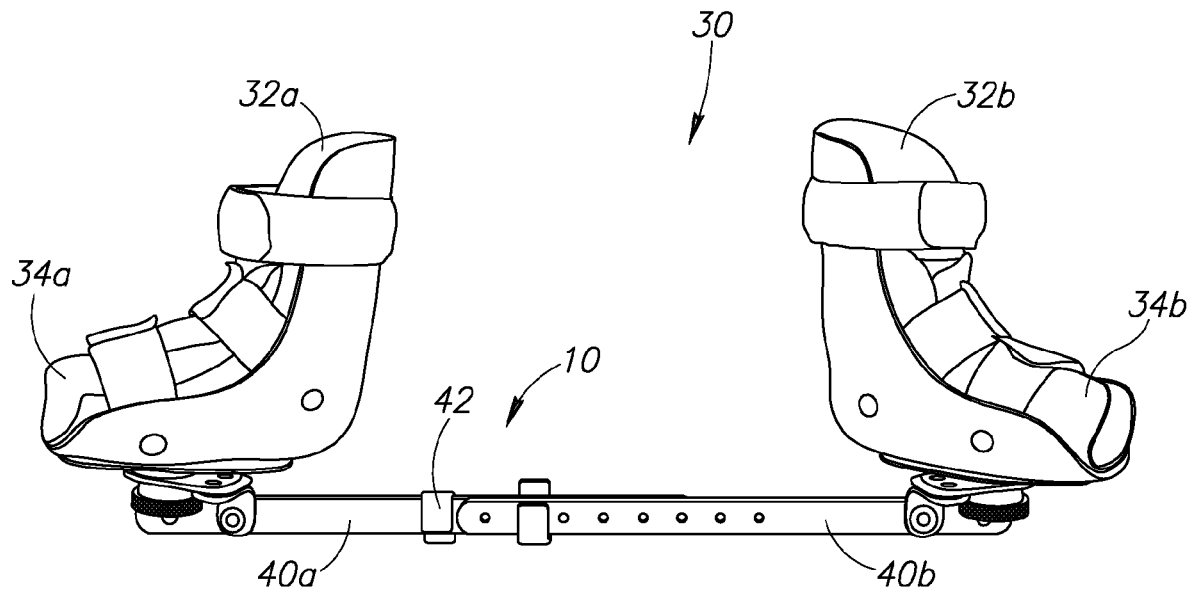
FIG. 5A is a front view of the orthotic device.
Figure 5B:
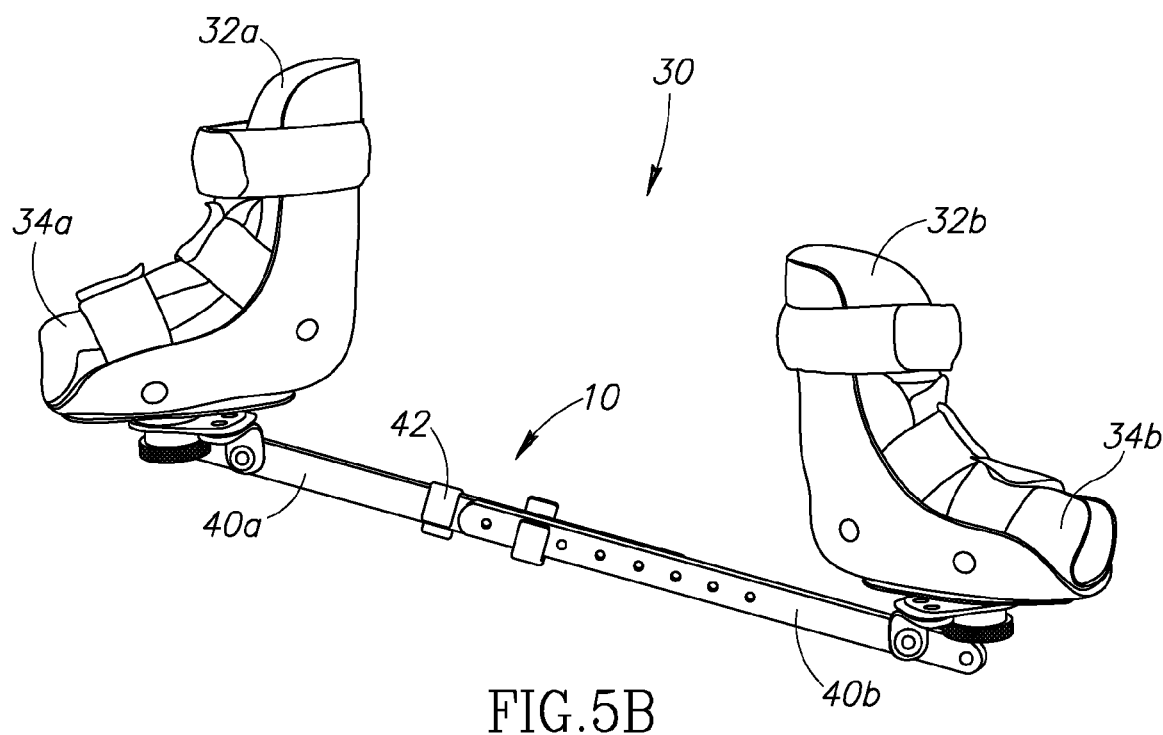
FIG. 5B is an alternative front view of the orthotic device.

Referring to the drawings in which like numerals represent like elements throughout the several views, a presently preferred embodiment of the orthotic device 60 of the present invention is depicted in FIGS. 1, 2, and 3, including an orthotic splint assembly 30, two ankle foot orthosis (AFO) 32a and 32b, and two custom molded inserts 34a and 34b secured thereto. Alternate views of an orthotic device 60 are shown in FIGS. 5A and 5B.

Figure 6A:
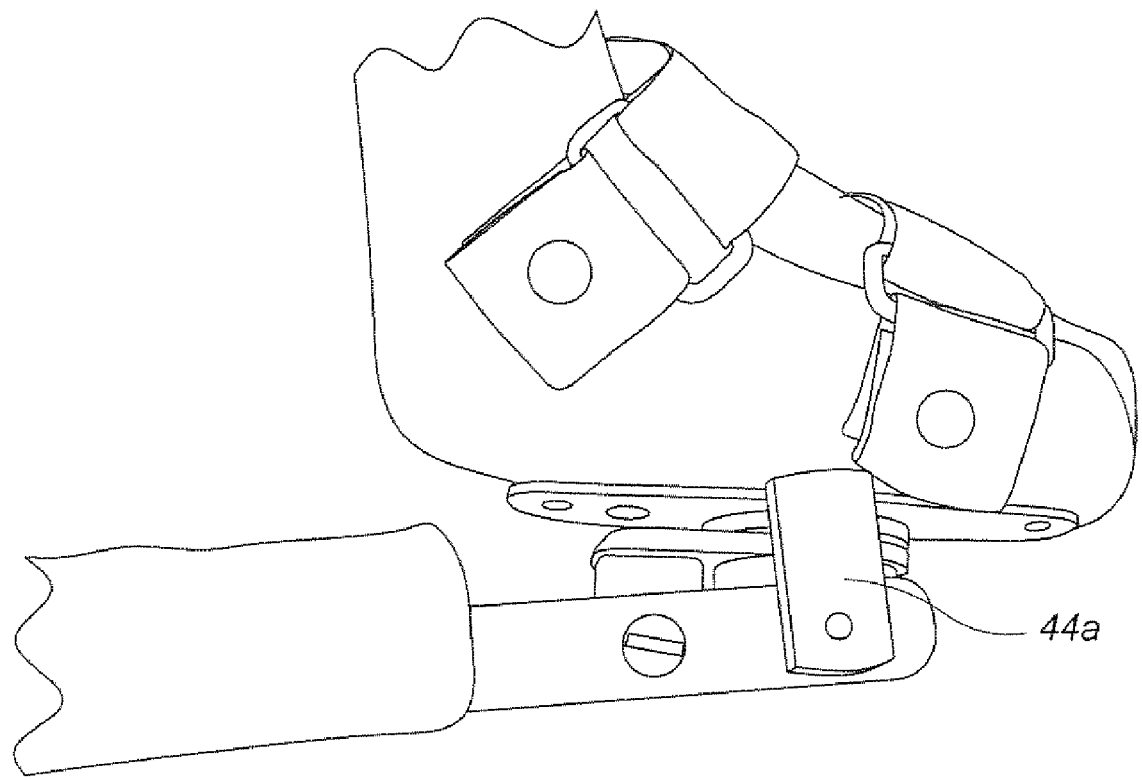
FIG. 6A is a side view of an embodiment of a foot support secured to the cross brace by a connecting member and a foot restraining member.
Figure 6B:
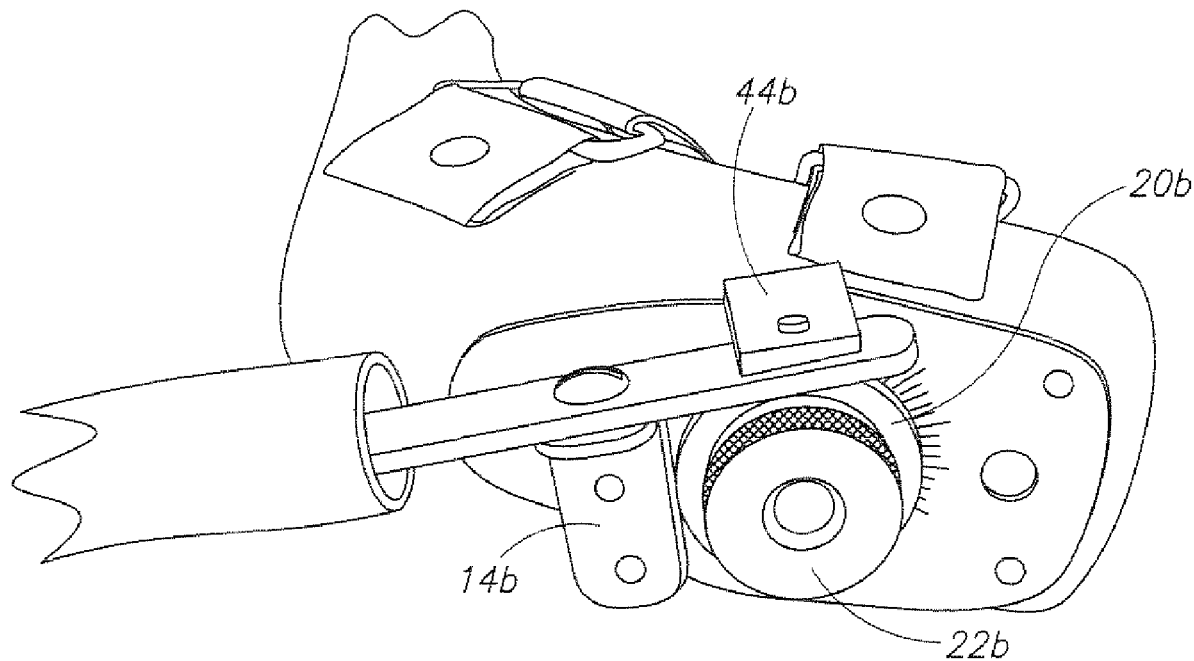
FIG. 6B is a bottom view of an embodiment of a foot support secured to the crossbrace by a connecting member and a foot restraining member.

As shown in FIG. 1, the orthotic splint assembly 30 includes a cross brace 10, two foot supports 12a and 12b, and two connecting members 14a and 14b interconnecting the cross brace 10 and each foot support 12a and 12b. Another view of an orthotic splint assembly 30 is shown on FIGS. 5A and 5B. Alternatively, the orthotic splint assembly may also include two foot restraining members 44a and 44b as shown on FIGS. 6A and 6B. The cross brace 10, the foot supports 12a and 12b, the connecting members 14a and 14b, and the foot restraining members 44a and 44b may each be made from a suitable metal or alloy, such as stainless steel, titanium, aluminum, aluminum alloy, or any other rigid material. Alternatively, the cross brace 10, the foot supports 12a and 12b, and connecting members 14a and 14b may be made of a suitable plastic, such as polypropylene, copolymer, or polyethylene. The cross brace 10, foot supports 12a and 12b, and connecting members 14a and 14b are preferably made from aluminum.

Figure 4A:
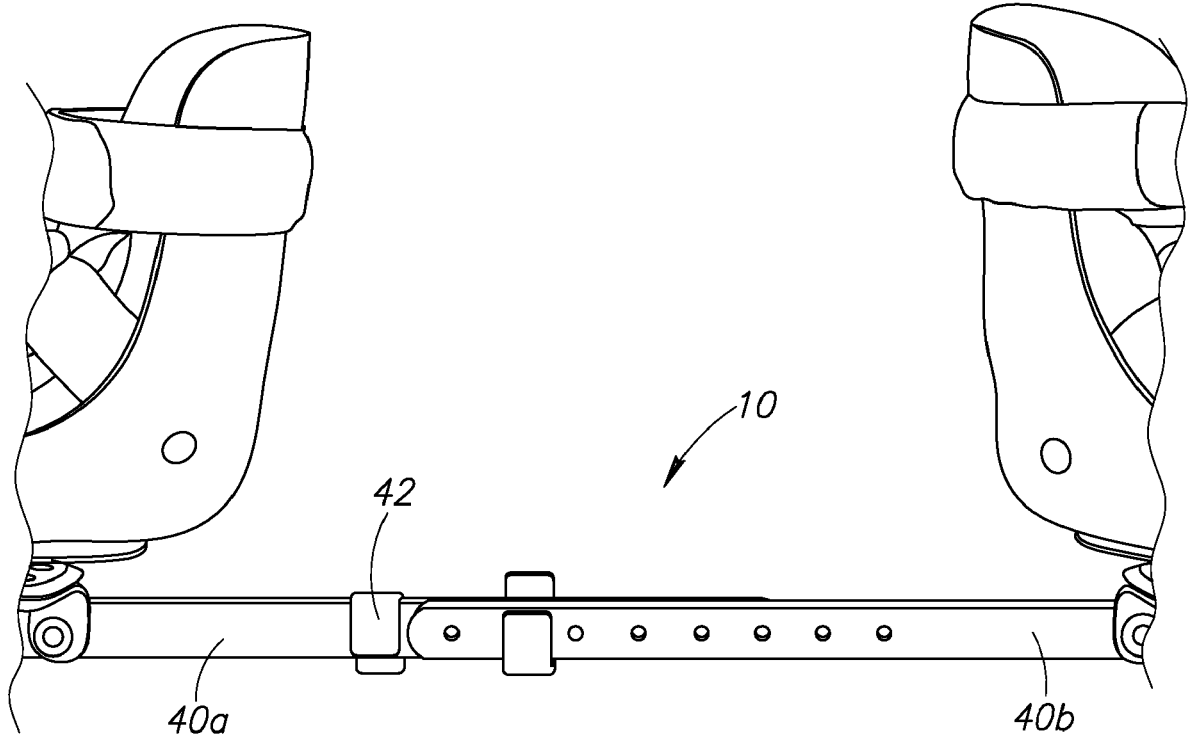
FIG. 4A is an expanded view of an optional quick disconnect for the cross brace.
Figure 4B:
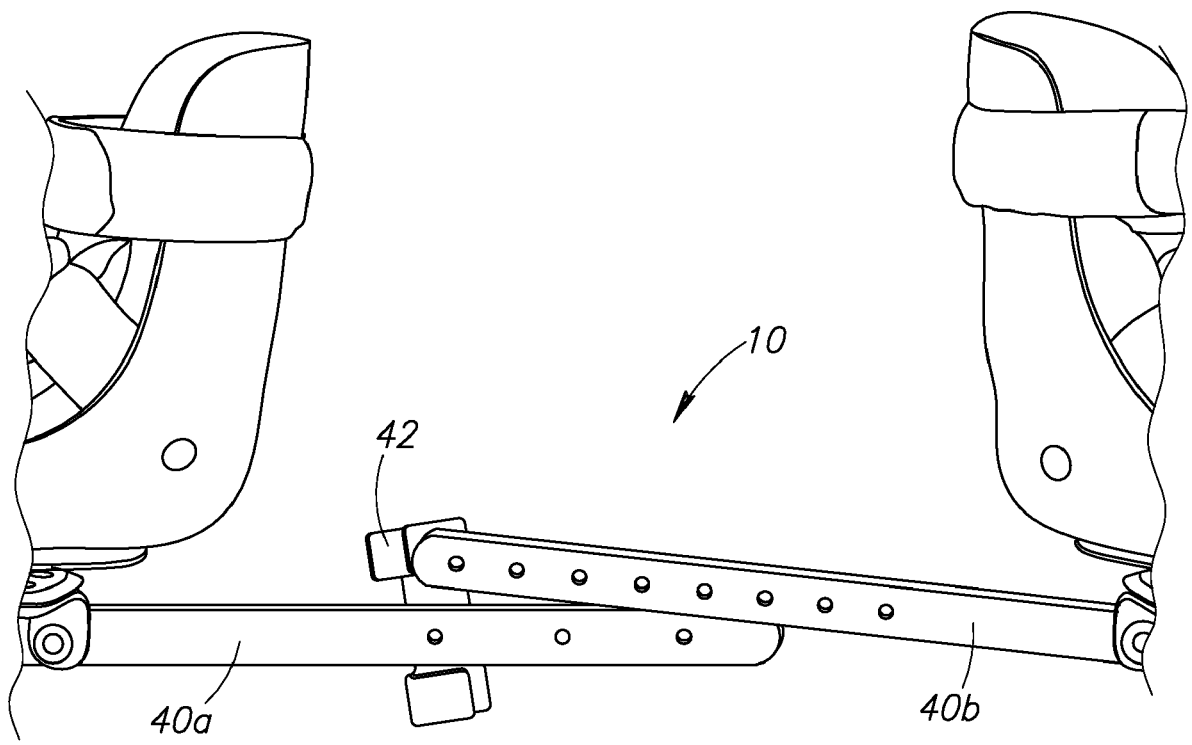
FIG. 4B is an alternative expanded view of the optional quick disconnect for the cross brace.

The cross brace is typically a linearly shaped member. In addition, the cross brace is preferably rigid. The cross brace 10 may be one piece or alternatively two pieces 40a and 40b that are each linearly shaped members secured by at least one adjusting means 42, as shown in FIGS. 4A and 4B. The adjusting means may be any type of adjusting means that would secure the two linearly shaped members so that the bar is rigid and can not slide in a horizontal axis, such as a clamp or a clip. The cross brace 10 may have a protective covering around it such as a fabric, padding, or styrofoam to protect the user. The cross brace maintains the foot supports approximately shoulder width apart, and as such, the length of the cross brace may vary depending on the patient. The cross brace may be from about 8 in to about 16 in length. The two-piece cross brace may be used as a quick disconnect as shown on FIG. 4B. The quick disconnect allows a parent or care-giver to separate the patient's feet if necessary, but would not allow the patient to separate his own feet or would not easily come apart on general use.

The connecting members 14a and 14b may be any type of connecting device that would secure the foot support to the cross brace, such as a right angle member or a bracket. Preferably, the connecting members 14a and 14b are right angle members. The connecting member 14a has one arm fixed to the foot support 12a and the other arm interconnected to the cross brace by a pivot assembly 16a. Preferably the connecting member 14a is connected directly to the support plate 20a on the foot support 12a. It will be understood that the other foot assembly 12b and the objects comprising it or connected thereto equally function as the ones described herein. The pivot assembly 16a may include any type of assembly that allows the foot support 12a to freely move or swivel about a vertical axis, while connected to the cross brace, such as a nut and bolt combination.

The foot restraining members 44a and 44may be any type of connecting device that would secure the foot support to the cross brace along with the connecting members 14a and 14b, preventing foot plantar flexion or extension of the patient's foot resulting in the forefoot moving away from the body. Preferably, the foot restraining members 44a and 44b are right angle members. The foot restraining member 44a has one arm perpendicularly affixed to the foot support 12a and the other arm non-movably fixed to the cross brace. Preferably, the foot restraining member 44a is connected directly to the orthosis support.

The foot support 12a includes an orthosis support 18a, a support plate 20a, and an adjusting member 22a. As shown on FIG. 2, the support plate 20a is secured to the orthosis support 18a by means if the adjusting member 22a. The adjusting member 22a may be a clamping shoulder screw or any other means used to secure the support plate 20a to the orthosis support 18a. The adjusting member 22a can be tightened or loosened to adjust the position of the orhtosis support 18a to the support plate 20a and allows the user to set the position of the patient's feet at a desired angle. In addition, the adjusting member 22a includes a stop assembly for selectively restricting the movement of the support plate in relation to the orthosis support to a pre-selected angle, usually approximately 30°, 45°, or 70°.

Alternatively the foot support 12a may comprise a detachable mechanism wherein the AFO 32a, 32b may be released from the foot support 12a by the parent or care-giver so as to free the patient from the orthotic splint assembly, if necessary. Such a mechanism may include an interlocking mechanism between the orthosis support 18a and the support plate 20a. Such a mechanism would also include a lever or releasing mechanism, which would release the orthosis support 18a from the support plate 20a. The orthosis support 18a may, for example contain one or a plurality of brackets or any other means of securing the orthosis support 18a to the support plate 20a. The support plate 20a may, for example, contain one or a plurality of attachments that would slide or hook into the brackets of the orthosis support 18a. Once the orthosis support 18a and support plate 20a are interconnected the two would only be released by the lever or releasing mechanism.

A further alternative is for the foot support 12a to be connected to the brace by an angle mechanism wherein the feet of the patient are kept with the toes pointing upward and the heels down. This alternative would maintain the patient's feet at the angle desired to continue to correct the clubfoot deformity. The angle mechanism may include, for example, an angled orthosis support and support plate, and angled connecting member, or another suitable way of maintaining the feet of the patient at the desired angle.

The AFO's 32a, 32b used in the prior art were uncomfortable and often caused the patient blister formation. The present invention, by using a custom molded insert cast from the wearer's own ankle and foot, is better suited to prevent blister formation and discomfort. By increasing user compliance, further surgery and complications may be avoided. As seen in FIG. 1, the orthotic device comprises the orthotic splint assembly 30 and two AFOs 32a and 32b. As seen in FIG. 3, each AFO 32a or 32b has a custom molded insert 34a that is placed inside the AFO 32a and thereafter secured thereto by a securing means 36. The AFO of the present invention is a standard AFO that is commercially available from Fillauer or American Prosthetic Components Inc., and is generally utilized to correct ankle and foot deformities. The AFOs 32a and 32b may be made from a suitable plastic, such as polypropylene, copolymer, or polyethylene and may be manufactured in any color or design pattern.

The AFO 32a is fixed to the orthosis support 18a of the orthotic splint assembly 30 by any method generally known in the art, such as screws, rivets, bolts, or adhesive. The AFO 32a is generally L-shaped and has an open front so that the custom molded insert 34a can be placed therein. The custom molded insert 34a is secured to the AFO 32a, such as straps, laces, VELCRO® straps, or any other conventional means. Preferably, the securing means 36 is a strap and hook to receive the strap. The custom molded insert 34a can be secured to the AFO 32a with a plurality of securing means 36a. Preferably, the securing means 36 are VELCRO® straps. More preferably, the AFO 32a extends higher than the calf and includes a strap around the lower leg to help keep the patient's feet in the brace.

To make the custom molded insert 34, a cast is made of the patient's foot and lower leg. After the cast is made, a suitable insert material is poured onto the cast and allowed to harden to the formed custom molded insert. The custom molded insert is lightweight and thin. The custom molded insert 34 may be made from a suitable material such as DURAFLEX, polyethylene, elastomeric gels. The custom molded insert 34a is generally L-shaped, extends from the patient's toes to the calf of the patient and has an open front to allow a patient's foot to be placed therein. As the custom molded insert 34a is made from the patient's own foot, it is comfortable to wear and prevents the formation of blisters on the patient's foot, which was one of the main problems with traditional bracing.

In view of the above, it will be seen that the several aspects of the invention are achieved and other advantageous results attained.

When introducing elements of the present invention or the preferred embodiment(s) thereof, the articles "a", "an", and "the" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. An orthotic splint assembly comprising:
   a rigid cross brace;
   a first connecting member connected to a first foot support, the first connecting member having one arm secured to the foot support and another arm interconnected to the cross brace by a first pivot assembly; and,
   a second connecting member connected to a second foot support, the second connecting member having one arm secured to the foot support and another arm interconnected to the cross brace by a second pivot assembly wherein the first and second foot support each comprises an orthosis support, a support plate, and an adjusting member, wherein the adjusting member comprises a stop assembly for selectively restricting the movement of the support plate in relation to the orthosis support to a pre-selected angle, the angle selected from the group consisting of approximately 30°, 45°, and 70°.

2. The orthotic splint assembly of claim 1, wherein the first and second pivot assembly allow each foot support to independently swivel around a vertical axis.

3. An orthotic splint assembly comprising:
   a rigid cross brace;
   a first connecting member connected to a first foot support, the first connecting member having one arm secured to the foot support and another arm interconnected to the cross brace by a first pivot assembly; and,
   a second connecting member connected to a second foot support, the second connecting member having one arm secured to the foot support and another arm interconnected to the cross brace by a second pivot assembly wherein the first and second foot support each comprises an orthosis support, a support plate, and an adjusting member, further comprising an ankle foot orthosis connected to each foot support and a custom molded insert secured inside the ankle foot orthosis by a securing means.

4. The orthotic splint assembly of claim 3, wherein the rigid cross brace comprises two linearly shaped members secured to each other by at least one adjusting means.

5. An orthotic splint assembly comprising:
   a rigid cross brace;
   a first connecting member connected to a first foot support, the first connecting member having one arm secured to the foot support and another arm interconnected to the cross brace by a first pivot assembly; and, a second connecting member connected to a second foot support, the second connecting member having one arm secured to the foot support and another arm interconnected to the cross brace by a second pivot assembly wherein the first and second foot support each comprises an orthosis support, a support plate, and an adjusting member, further comprising:
   a first foot restraining member connected to a first foot support, the first foot restraining member having one arm secured to the foot support and another arm non-movably fixed to the cross brace; and,
   a second foot restraining member connected to a second foot support, the second foot restraining member having one arm secured to the foot support and another arm non-movably fixed to the cross brace, whereby the first and second foot restraining members prevent foot plantar flexion.

6. An orthotic device comprising:
   a rigid cross brace;
   a first connecting member connected to a first foot support, the first connecting member having one arm secured to the first foot support and another interconnected to the cross brace by a first pivot assembly;
   a second connecting member connected to a second foot support, the second connecting member having one arm secured to the second foot support and another arm interconnected to the cross brace by a second pivot assembly;
   an ankle foot orthosis connected to each of said first and second foot supports; and,
   a custom molded insert secured inside the ankle foot orthosis by a securing means, wherein the first and second foot supports each comprise an orthosis support, a support plate, and an adjusting member.

7. The orthotic device of claim 6, wherein the adjusting member comprises a stop assembly for selectively restricting the movement of the support plate in relation to the orthosis support to a pre-selected angle, the angle selected from the group consisting of approximately 30°, 45°, and 70°.

8. The orthotic device of claim 6, wherein the first pivot assembly and the second pivot assembly allow each of said first and second foot supports to independently swivel around a vertical axis.

9. The orthotic device of claim 6, wherein the rigid cross brace comprises two linearly shaped members secured to each other by at least one adjusting means.

10. The orthotic device of claim 6, further comprising:
   a first foot restraining member connected to a first foot support, the first foot restraining member having one arm secured to the first foot support and the other arm non-movably fixed to the cross brace; and,
   a second foot restraining member connected to a second foot support, the second foot restraining member having one arm secured to the second foot support and the other arm non-movably fixed to the cross brace, whereby the first and second foot restraining members prevent foot plantar flexion.

11. An orthotic device for the correction of deformed feet comprising:
   a rigid cross brace, said rigid cross brace defining a linearly shaped member;
   a pair of opposed foot supports, each of said pair of opposed foot support being operatively engaged to either end of said linearly shaped member;
   an ankle foot orthosis connected to each of said opposed pair of opposed foot supports; and,
   a custom molded insert secured to each ankle foot orthosis by a securing means, wherein each foot support comprises an orthosis support, a support plate, and an adjusting member, wherein said adjusting member comprises a stop assembly for selectively restricting the movement of the support plate in relation to the orthosis support to a pre-selected angle, the angle selected from the group consisting of approximately 30°, 45°, and 70°, wherein the each of said pair of foot supports is connected to said rigid cross brace by a connecting member.

12. An orthotic device for the correction of deformed feet comprising:
   a rigid cross brace, said rigid cross brace defining a linearly shaped member;
   a pair of opposed foot supports, each of said pair of opposed foot support being operatively engaged to either end of said linearly shaped member;
   an ankle foot orthosis connected to each of said opposed pair of opposed foot supports; and,
   a custom molded insert secured to each ankle foot orthosis by a securing means, wherein each foot support comprises an orthosis support, a support plate, and an adjusting member, wherein said adjusting member comprises a stop assembly for selectively restricting the movement of the support plate in relation to the orthosis support to a pre-selected angle, the angle selected from the group consisting of approximately 30°, 45°, and 70°, wherein the connecting member is a right angle member.

13. An orthotic device for the correction of deformed feet comprising:
   a rigid cross brace, said rigid cross brace defining a linearly shaped member;
   a pair of opposed foot supports, each of said pair of opposed foot support being operatively engaged to either end of said linearly shaped member;
   an ankle foot orthosis connected to each of said opposed pair of opposed foot supports; and,
   a custom molded insert secured to each ankle foot orthosis by a securing means, wherein each foot support comprises an orthosis support, a support plate, and an adjusting member, wherein said adjusting member comprises a stop assembly for selectively restricting the movement of the support plate in relation to the orthosis support to a pre-selected angle, the angle selected from the group consisting of approximately 30°, 45°, and 70°, wherein said right angle member has one arm secured to one of said opposed foot supports and an other arm interconnected to said cross brace by a pivot assembly.

14. An orthotic device for the correction of deformed feet comprising:
   a rigid cross brace, said rigid cross brace defining a linearly shaped member
   a pair of opposed foot supports, each of said pair of opposed foot support being operatively engaged to either end of said linearly shaped member:
   an ankle foot orthosis connected to each of said opposed pair of opposed foot supports; and,
   a custom molded insert secured to each ankle foot orthosis by a securing means, wherein each foot support comprises an orthosis support, a support plate, and an adjusting member, wherein said adjusting member comprises a stop assembly for selectively restricting the movement of the support plate in relation to the orthosis support to a pre-selected angle, the angle selected from the group consisting of approximately 30°, 45°, and 70°, wherein the rigid cross brace comprises two linearly shaped members secured to each other by at least one adjusting means.

* * * * *

UNITED STATES PATENT AND TRADEMARK OFFICE
CERTIFICATE OF CORRECTION

| | |
|---|---|
| PATENT NO. | : 7,569,023 B2 |
| APPLICATION NO. | : 11/426376 |
| DATED | : August 4, 2009 |
| INVENTOR(S) | : Matthew Dobbs |

It is certified that error appears in the above-identified patent and that said Letters Patent is hereby corrected as shown below:

Claim 6, col. 6, line 57: "another interconnected" should read --another arm interconnected--

Signed and Sealed this
Fourteenth Day of February, 2012

David J. Kappos
*Director of the United States Patent and Trademark Office*